US006673045B1

(12) United States Patent
Kraus

(10) Patent No.: US 6,673,045 B1
(45) Date of Patent: Jan. 6, 2004

(54) FLOW INDICATORS FOR AMBULATORY INFUSION

(76) Inventor: Menachem A. Kraus, 25 Pashosh Street, Rehovot 26824 (IL)

( * ) Notice: Subject to any disclaimer, the term of this patent is extended or adjusted under 35 U.S.C. 154(b) by 0 days.

(21) Appl. No.: 09/402,991

(22) PCT Filed: Mar. 24, 1998

(86) PCT No.: PCT/IL98/00132
§ 371 (c)(1),
(2), (4) Date: Jan. 6, 2000

(87) PCT Pub. No.: WO98/46291
PCT Pub. Date: Oct. 22, 1998

(30) Foreign Application Priority Data

Apr. 17, 1997 (IL) .................................................. 120693

(51) Int. Cl.$^7$ ............................ A61M 1/00; A61M 5/00; A61M 5/14
(52) U.S. Cl. ........................................ 604/126; 604/251
(58) Field of Search ......................... 604/9, 30, 99.03, 604/99.02, 126, 131, 167.02, 167.03, 186, 190, 236, 247, 213, 251, 252, 254; 210/94, 436; 96/6

(56) References Cited

U.S. PATENT DOCUMENTS 3,744,492 A    7/1973  Leibinsohn ............ 128/214 C
3,993,066 A *  11/1976 Virag ........................... 604/86
4,116,646 A    9/1978  Edwards ....................... 55/159
4,173,222 A *  11/1979 Muetterties .................. 128/214
4,278,084 A *  7/1981  Pope, Jr. ..................... 604/406
4,316,460 A    2/1982  Genese et al. ............ 128/214 R
4,396,016 A *  8/1983  Becker ........................ 604/126
4,447,230 A    5/1984  Gula et al. .................. 604/122
4,521,212 A *  6/1985  Ruschke ...................... 604/126
4,906,260 A *  3/1990  Emheiser et al. ............ 210/445

FOREIGN PATENT DOCUMENTS

WO    WO 96/29104    9/1996
WO    WO 96/34651    11/1996

* cited by examiner

Primary Examiner—Brian L. Casler
Assistant Examiner—Matthew DeSanto
(74) Attorney, Agent, or Firm—David Klein; Dekel Patent Ltd.

(57) ABSTRACT

An intravenous infusion flow indicator including a housing defining an infusion liquid inlet and an infusion liquid outlet, a hydrophilic membrane disposed in the housing and being operative, when wetted, for permitting liquid flow and preventing air flow therethrough to the liquid outlet, wherein the liquid flow may be observed as droplets, the housing defining at least one volume, whose size and configuration are selected such that irrespective of the orientation of the housing following priming, infusion liquid within the housing is always in touching relationship with the membrane, thereby permitting continued infusion liquid flow therethrough.

16 Claims, 10 Drawing Sheets

FLOW INDICATORS FOR AMBULATORY INFUSION

FIELD OF THE INVENTION

The present invention relates generally to flow indicators for intravenous infusion devices.

BACKGROUUND OF THE INVENTION

Intravenous infusion devices are employed in both hospital and home environments. In all environments, it is essential to monitor continuity of flow, since discontinuity in flow can have extremely serious consequences for the health of a patient receiving an intravenous infusion.

In a hospital environment, intravenous infusion is either gravity or pump driven. Gravity driven devices typically include drip chambers which enable flow to be monitored by professional staff. Pump driven devices typically include various displays and alarms which indicate flow discontinuities.

In a home environment, there are known various electronic pumps as well as disposable mechanical devices such as elastomeric infusers and spring loaded mechanisms. Examples of such devices include the Infusor device marketed by Baxter Healthcare and the Paragon device marked by I-Flow. Devices of this type often operate at extremely low flow rates as slow as 0.5 ml/hr. Flow indications are provided either by volume gradations or a dipstick-like device, however, due to the low flow rates, resulting in small changes in volume, it may take a long time, up to 15–30 minutes or more, to observe a volume change.

The lack of a reliable and quick way to ascertain flow continuity is an important shortcoming of currently available infusion devices for home use and is a known cause of anxiety in home patients.

Published PCT application WO 96/34651 describes a highly complex mechanical construction for indicating flow in a disposable infusion device at specific rates over extended periods of time.

Drip chambers are conventionally employed to detect infusion flow. They are not normally suitable for use in ambulatory infusion because when they are oriented horizontally or upside-down they may release trapped air into the infusion line which both endangers the patient and renders the drip chamber inoperable, since it fills with liquid.

Applicant/Assignee's copending Published PCT application WO 96/29104 describes a drip chamber which does not lose air due to the provision of a hydrophilic membrane positioned at the outlet. The membrane allows free passage of liquid therethrough but prevents air passage therethrough at all pressures below the bubble point of the membrane.

Although it has an important advantage in preventing air intrusion into the infusion line, the drip chamber of application WO 96/29104 is nevertheless inoperable in an upside-down orientation because air comes into contact with the membrane and ceases flow.

SUMMARY OF THE INVENTION

The present invention seeks to provide a simple to use, inexpensive and efficient intravenous infusion flow indicator, which is capable of demonstrating flow at even the lowest infusion rates commonly used and which does not require observation time exceeding about 30 seconds.

There is thus provided in accordance with a preferred embodiment of the present invention an intravenous infusion flow indicator including a housing defining an infusion liquid inlet and an infusion liquid outlet, a hydrophilic membrane disposed in the housing and being operative, when wetted, for permitting liquid flow and preventing air flow therethrough to the liquid outlet, the housing defining at least one volume, whose size and configuration are selected relative to the pressure of the infusion liquid at the infusion liquid inlet such that irrespective of the orientation of the housing following priming, infusion liquid within the housing is always in wetting relationship with the membrane, thereby permitting continued infusion liquid flow therethrough.

In accordance with a preferred embodiment of the present invention, the housing defines first and second volumes communicating with each other, the first volume being greater than the second volume, the configuration and the sizes of the first and second volumes being selected such that when the housing is in an upright configuration, the second volume is generally filled with air such that drops falling therethrough can be readily viewed for monitoring.

In accordance with one embodiment of the invention, the membrane has generally disc shape, the first volume has a generally flat cylindrical configuration and the second volume has a generally cylindrical configuration which is narrower and taller than the first volume.

In accordance with another embodiment of the invention, the membrane has a generally ring shape, the first volume has a generally top hat shape including a narrow high portion and a broad flat portion adjacent the membrane and the second volume has a generally cylindrical configuration similar to that of the narrow high portion.

In accordance with a preferred embodiment of the present invention, the infusion liquid is supplied through a narrow diameter liquid inlet, providing small drops in relatively quick succession, thus enabling the observation of flow rates as low as 0.5 ml/hr. For example, an inlet tube of inner diameter of 0.2 mm may be employed.

Additionally in accordance with a preferred embodiment of the present invention the membrane has a generally ring shape, the first volume and second volumes have generally semi-ellipsoidal configurations and the second volume is generally cylindrical of larger size than the first volume.

Further in accordance with a preferred embodiment of the present invention the membrane has a generally ring shape, the first volume has a generally semi-ellipsoidal shape and a broad flat portion adjacent the membrane and the second volume has a generally semi-ellipsoidal configuration.

Additionally in accordance with a preferred embodiment of the present invention the housing comprises a first element and a second element, wherein the second element includes a shoulder portion, and a diameter of the first element is chosen so as to define a volume when the first element and the second element are sealingly joined together.

There is also provided in accordance with a preferred embodiment of the present invention a method for indicating an intravenous infusion flow including providing a housing defining an infusion liquid inlet and an infusion liquid outlet and a hydrophilic membrane disposed in the housing and being operative, when wetted, for permitting liquid flow and preventing air flow therethrough to the liquid outlet, the housing defining at least one volume, whose size and configuration are selected such that irrespective of the orientation of the housing following priming, infusion liquid within the housing is always in touching relationship with the membrane, thereby permitting continued infusion liquid flow therethrough; priming said membrane with infusion liquid for full wetting thereof, and supplying infusion liquid under controlled pressure via said housing and said membrane to a patient.

Further in accordance with a preferred embodiment of the present invention the housing defines first and second volumes communicating with each other, the first volume being greater than the second volume, the configuration and the sizes of the first and second volumes being selected such that when the housing is in an upright configuration, the second volume is generally filled with air such that drops falling therethrough can be readily viewed for monitoring.

Still further in accordance with a preferred embodiment of the present invention the membrane has a generally disc shape, the first volume has a generally flat cylindrical configuration and the second volume has a generally cylindrical configuration which is narrower and taller than the first volume.

Additionally in accordance with a preferred embodiment of the present invention the membrane has a generally ring shape, the first volume has a generally top hat shape including a narrow high portion and a broad flat portion adjacent the membrane and the second volume has a generally cylindrical configuration similar to that of the narrow high portion.

Moreover in accordance with a preferred embodiment of the present invention the infusion liquid is supplied to the liquid inlet via narrow diameter tubing, providing small drops in relatively quick succession, thus enabling the observation of flow rates as low as 0.5 ml/hr.

BRIEF DESCRIPTION OF THE DRAWING

The present invention will be understood and appreciated more fully from the following detailed description, taken in conjunction with the drawings in which.

DETAILED DESCRIPTION OF PREFERRED EMBODIMENTS

Figure 1:
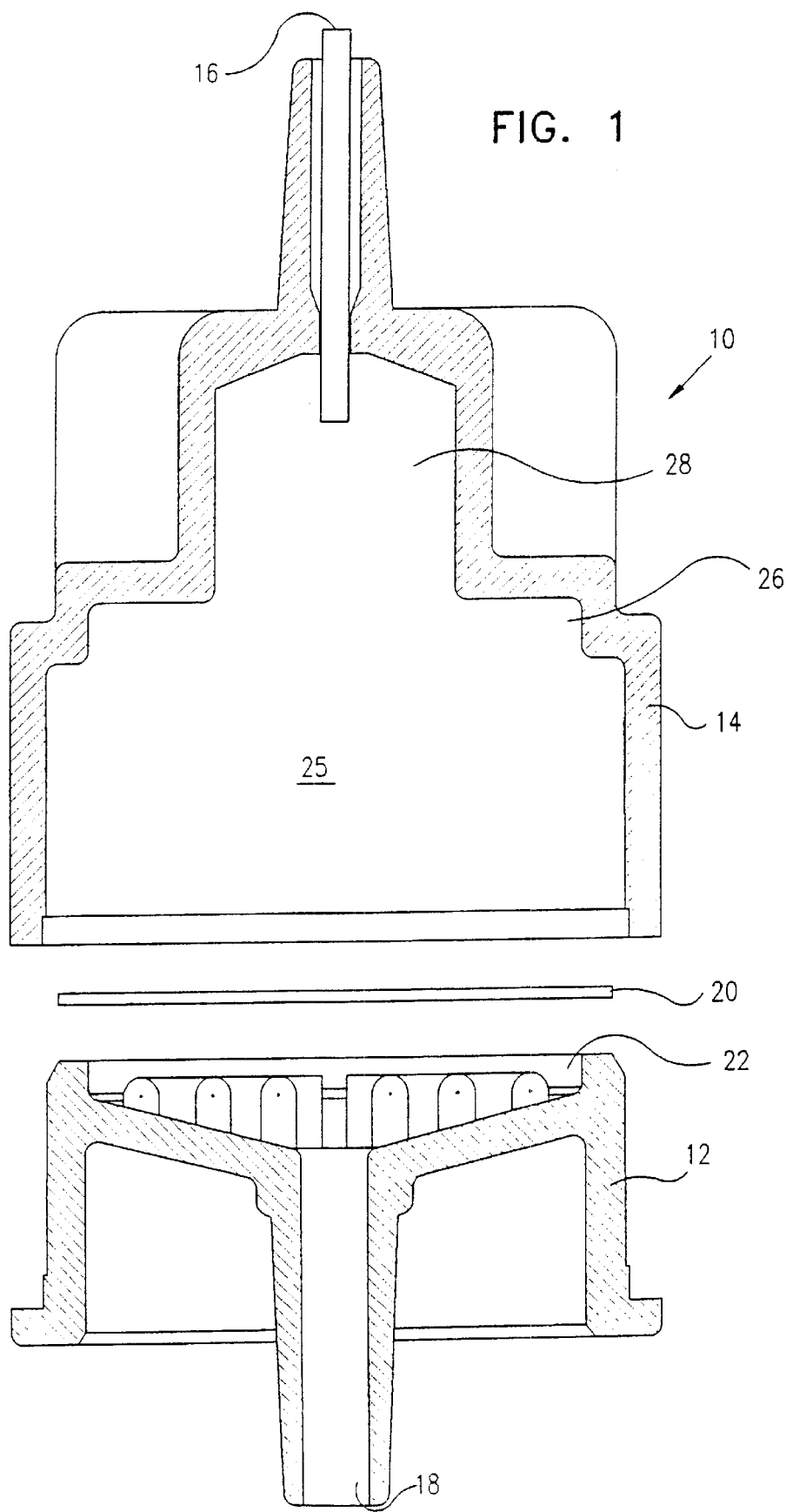
FIG. 1 is an exploded view pictorial illustration of an infusion flow indicator constructed and operative in accordance with a preferred embodiment of the present invention.
Figure 2:
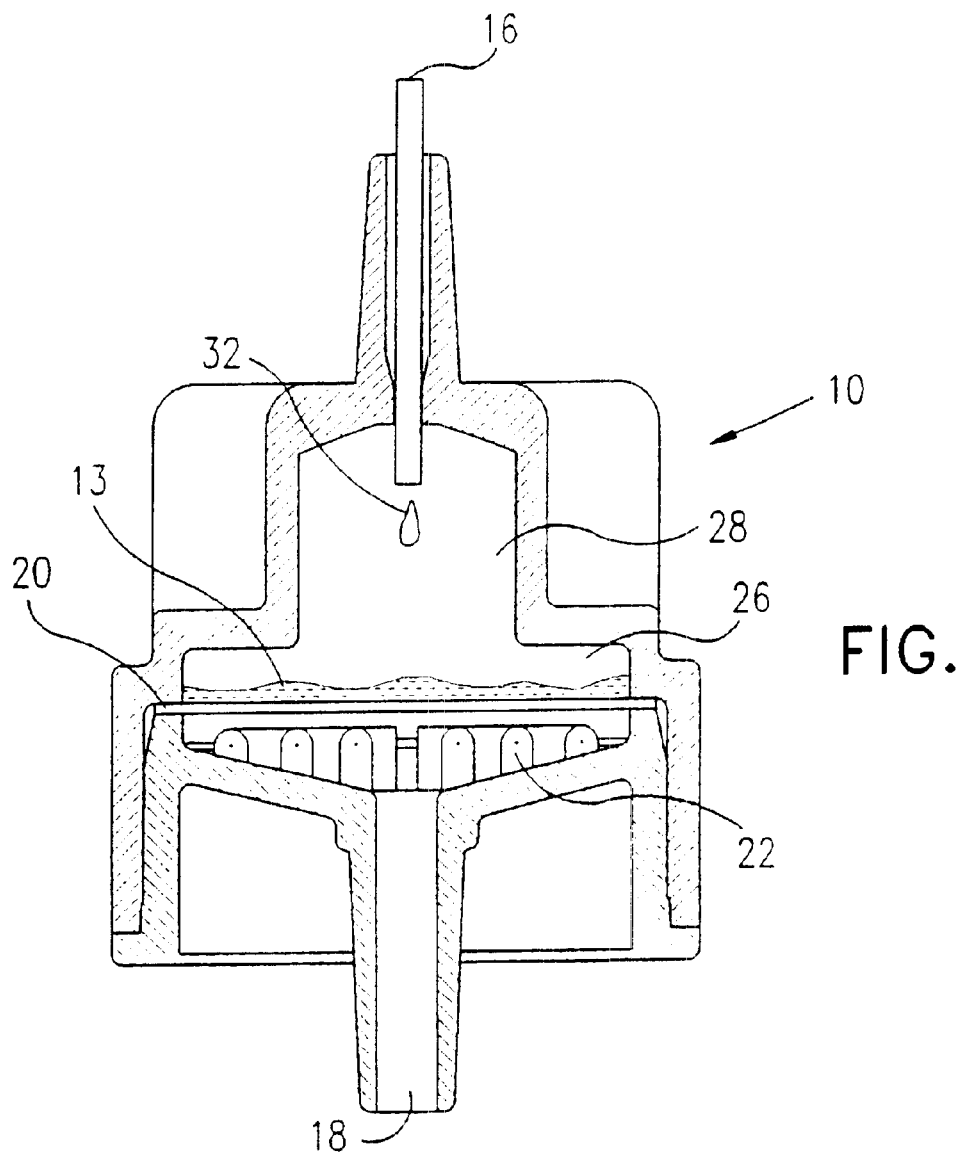
FIG. 2 is a sectional illustration of the flow indicator of FIG. 1 during priming.

Reference is now made to FIG. 1, which is an exploded view pictorial illustration of an infusion flow indicator constructed and operative in accordance with a preferred embodiment of the present invention and to FIG. 2, which is a sectional illustration of the flow indicator of FIG. 1 during priming.

The flow indicator of FIGS. 1 and 2 preferably comprises a housing indicated generally by reference numeral 10, and comprising first and second elements 12 and 14, respectively, sealingly joined together by, as is known in the art, and defining an infusion liquid inlet 16 and an infusion liquid outlet 18.

Disposed within housing 10 is a hydrophilic membrane 20 which is operative, when wetted, for permitting the flow of infusion liquid 13 and preventing air flow therethrough to the liquid outlet 18. The membrane 20 is preferably sealed to a membrane support 22, which is integrally formed with element 12.

In accordance with a preferred embodiment of the present invention, the housing 10 defines an interior volume 25, whose size and configuration are selected relative to the pressure of the infusion liquid 13 at the infusion liquid inlet 16 such that irrespective of the orientation of the housing following priming, infusion liquid 13 within the housing 10 is always in wetting relationship with the membrane 20, thereby permitting continued infusion liquid flow 13 therethrough.

In the illustrated embodiment, the interior volume 25 includes first and second volume portions 26 and 28. Volume portion 26 is preferably of generally flat cylindrical configuration and the second volume 28 has a generally cylindrical configuration which is narrower and taller than the first volume. The membrane 20 is preferably of a disc-shaped configuration.

The operation of the embodiment of FIGS. 1 and 2 will now be described with additional reference to FIGS. 3A–3C. Prior to use, the flow indicator must be primed with infusion liquid 13. In the present embodiment, during priming, the flow indicator is orientated in an upright position, as illustrated in FIG. 2. During priming, the driving force which drives the infusion liquid 13, such as that produced by an elastomeric bladder, spring, compressed gas or equivalent device, forces the infusion liquid 13 through liquid inlet 16 into volume 25.

At first, prior to complete wetting of the membrane 20, both air and liquid pass through the membrane 20 and liquid outlet 18. Once the membrane 20 is fully wetted, the air remaining in volume 25 cannot pass through the membrane 20 and thus becomes trapped in volume 25. The trapped air is subsequently compressed and the liquid level in the volume 25 rises. This continues until equilibrium is reached, when the pressure within volume 25 equals the liquid inlet pressure produced by the driving force. In bladder type infusion devices, this equilibrium is reached at a pressure of about 0.6 atmospheres.

In accordance with a preferred embodiment of the present invention, the volume size of portion 28 is chosen so that it is slightly less than about 40% of the total volume 25, and the volume size of portion 26 is slightly larger than approximately 60% of the total volume 25. Thus, after priming and pressure equilibration, the housing 10, contains approximately 40% liquid and approximately 60% air.

Figure 3A:
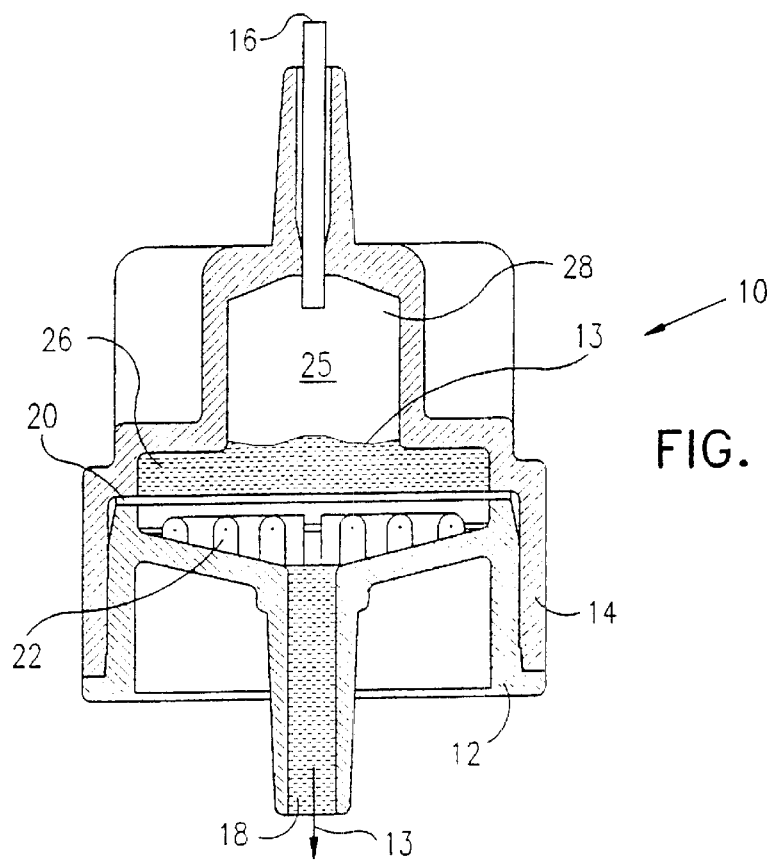
FIGS. 3A, 3B, and 3C are sectional illustrations of the flow indicator of FIGS. 2 and 3, following priming, in respective upright, upside-down and generally horizontal orientations.
Figure 3B:
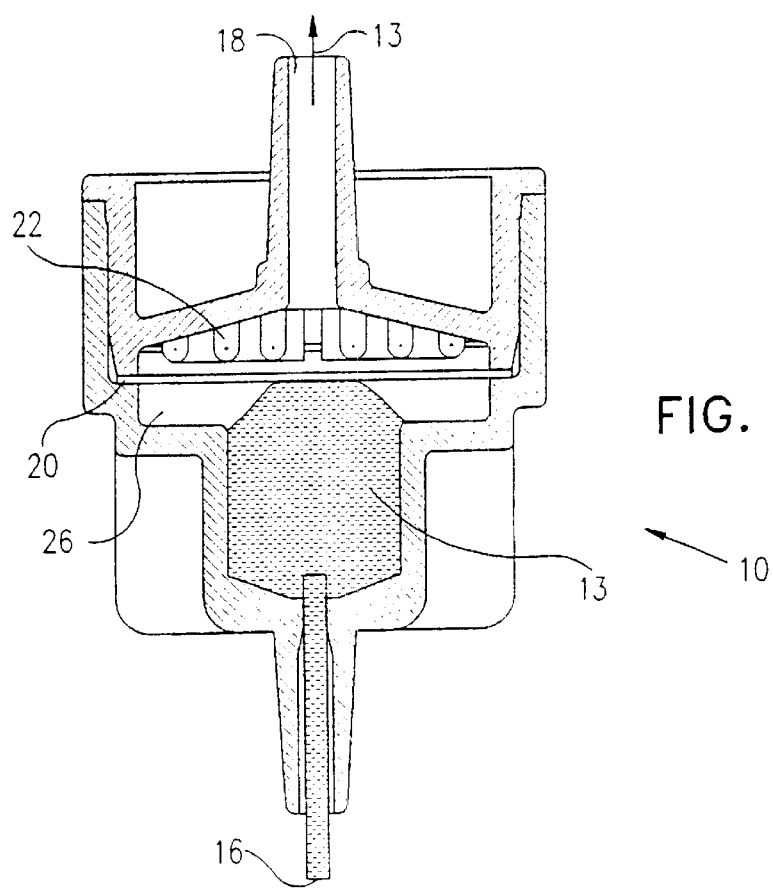

On turning the flow indicator upside down, FIG. 3B, volume 28 overfills The height and diameter of volumes 26 and 28 are chosen such that upon overfilling, the liquid 13 contacts the membrane 20 as illustrated in FIG. 3B.

FIG. 3A illustrates the housing 10 in an upright orientation. FIGS. 3B and 3C show the housing 10 in an upside-down and generally horizontal orientation, respectively. These drawings demonstrate that the flow of the infusion liquid is maintained independently of the orientation of the flow indicator.

More generally, it is a particular feature of the present invention that volume 25 is configured that at equilibrium, the infusion liquid 13 is in contact with the membrane 20 for maintaining full wetting thereof irrespective of the orientation of the housing 10. This feature ensures that when an infusion is being administered to an ambulatory patient and the infusion flow indicator may assume any orientation, the flow is not interrupted.

Figure 3C:
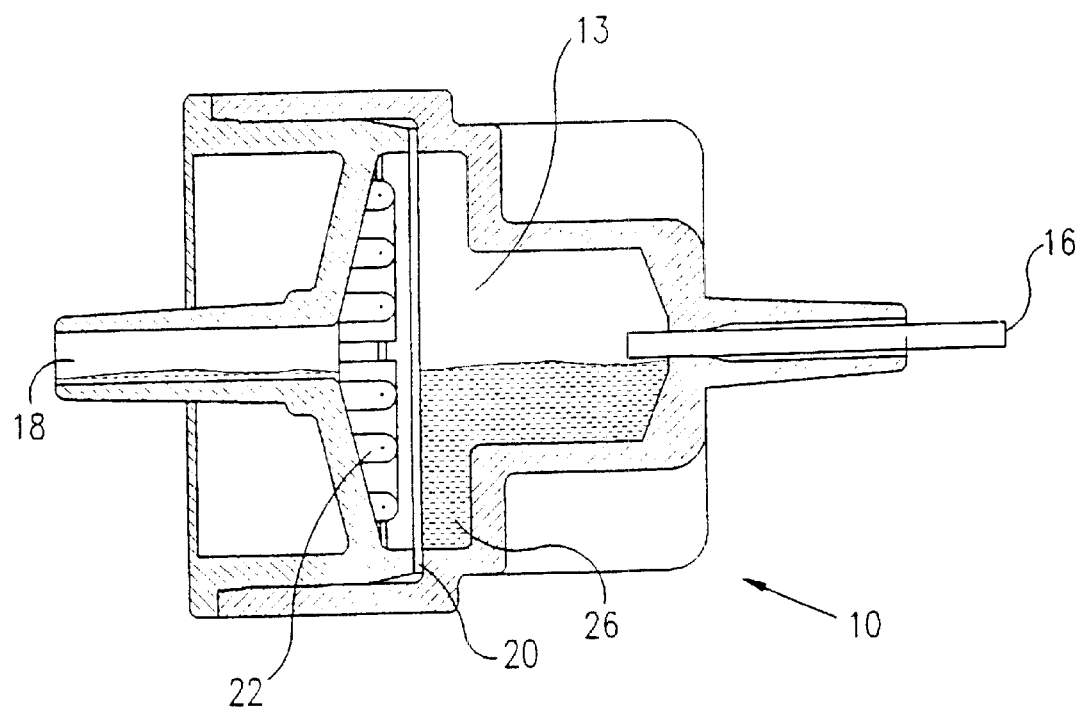

Reference is now made to FIGS. 3A, 3B and 3C which illustrate the flow indicator of FIGS. 1 and 2, following priming, in respective upright, upside-down and generally horizontal orientations. It can be seen that in all of the illustrated orientations, the infusion liquid is in contact with the membrane 20.

In accordance with a preferred embodiment of the present invention, the infusion liquid 13 is supplied to the narrow liquid inlet 16, providing small drops 32 in relatively quick succession (FIG. 2), thus enabling the observation of flow rates as low as 0.5 ml/hr. For example, an inlet tube of an inner diameter of 0.2 mm may be employed.

Figure 4:
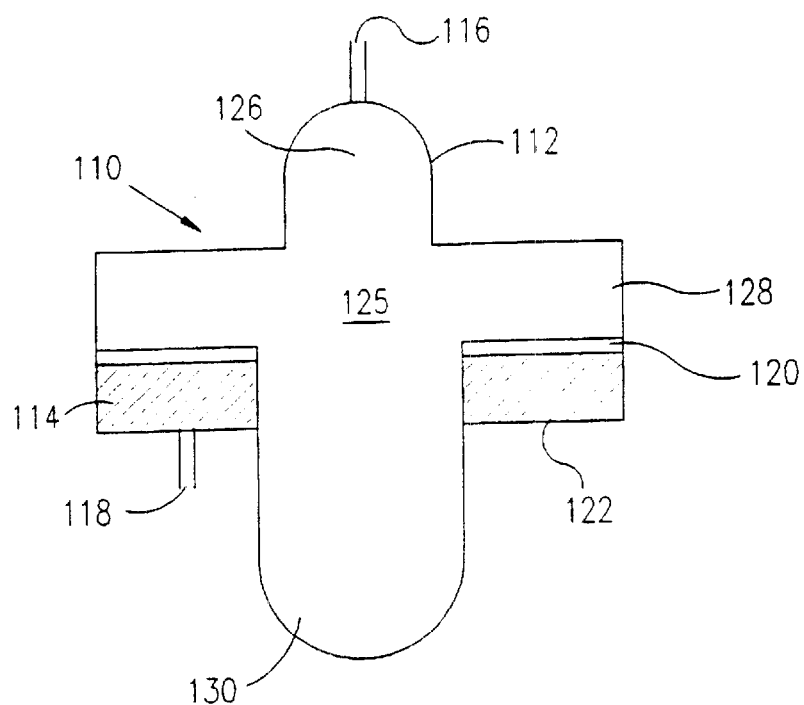
FIG. 4 is a sectional illustration of an infusion flow indicator constructed and operative in accordance with another preferred embodiment of the present invention.

Reference is now made to FIG. 4 which is an illustration of an infusion flow indicator constructed and operative in accordance with another preferred embodiment of the present invention.

The flow indicator of FIG. 4 preferably comprises a housing 110, a first element 112 and second element 114, sealingly joined together, as is known in the art, and defining a narrow infusion liquid inlet 116 and an infusion liquid outlet 118. The housing 110 defines an internal volume 125.

Within the housing 110 is disposed a hydrophilic membrane 120, and is preferably in the form of a ring. The membrane 120 is operative, when wetted, for permitting infusion liquid flow and preventing air flow through the housing 110 to the liquid outlet 118. The membrane 120 is preferably sealed to a membrane support 122.

As shown in FIG. 4, the volume 125 comprises a first volume 126 and a second volume 130. The first volume 126 is preferably of semi-ellipsoidal shape with a base section 128 of generally flat cylindrical configuration. The second volume 130 is preferably of semi-ellipsoidal shape, and being generally of larger volume than the first volume 126. Volume 130 is larger than the sum of volumes 126 and 128.

Figure 5:
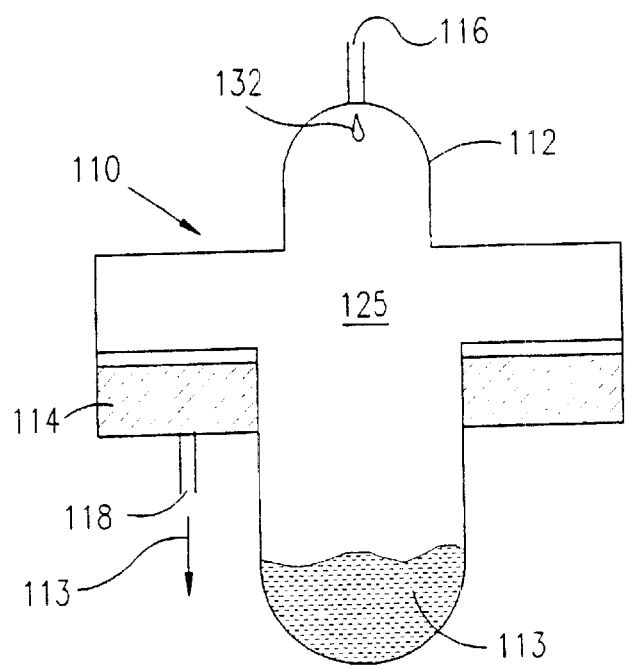
FIG. 5 is a sectional illustration of the flow indicator of FIG. 4 during priming.

In the present embodiment, during priming, the flow indicator is orientated in an upright position, as illustrated in FIG. 5.

During the priming operation, the infusion liquid 113 is supplied to the narrow liquid inlet 116, providing small drops 132 in relatively quick succession. The liquid 113 fills the second volume 130 until the membrane 120 is covered by liquid 113 and liquid contact is established with membrane 120. The filling process is continued until equilibrium is reached and the pressure within the volume 125 equals the liquid inlet pressure.

Figure 6A:
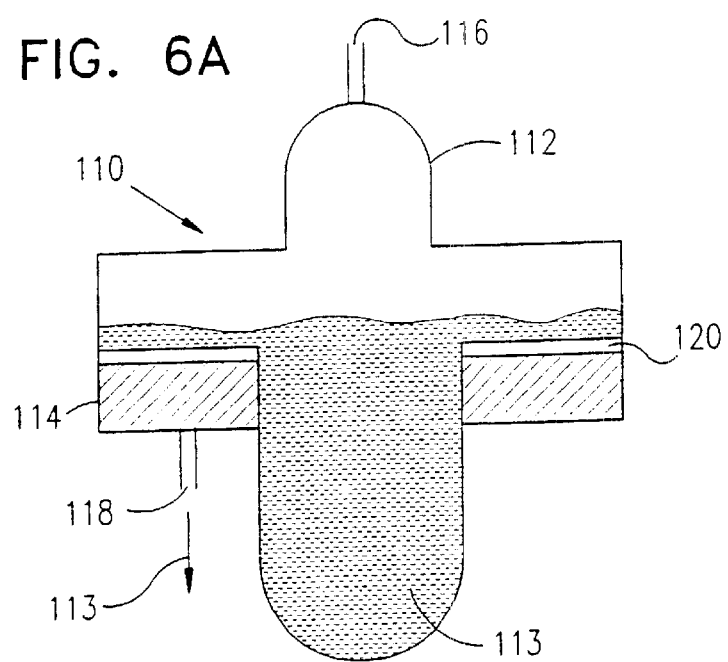
FIGS. 6A, 6B, and 6C are sectional illustrations of the flow indicator of FIGS. 4 and 5, following priming, in respective upright, upside-down and generally horizontal orientations.

In operation of the embodiment of FIGS. 4 and 5, the infusion liquid 113 permeates through the membrane 120 and exits the housing 110 through the liquid outlet 118, as illustrated in FIG. 6A.

Figure 6B:
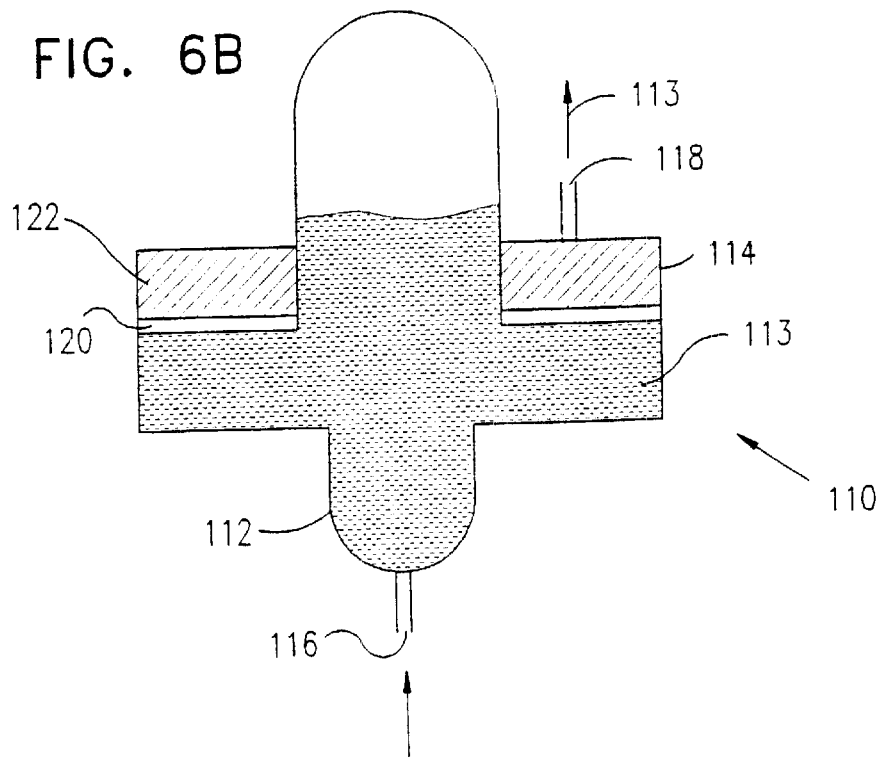
Figure 6C:
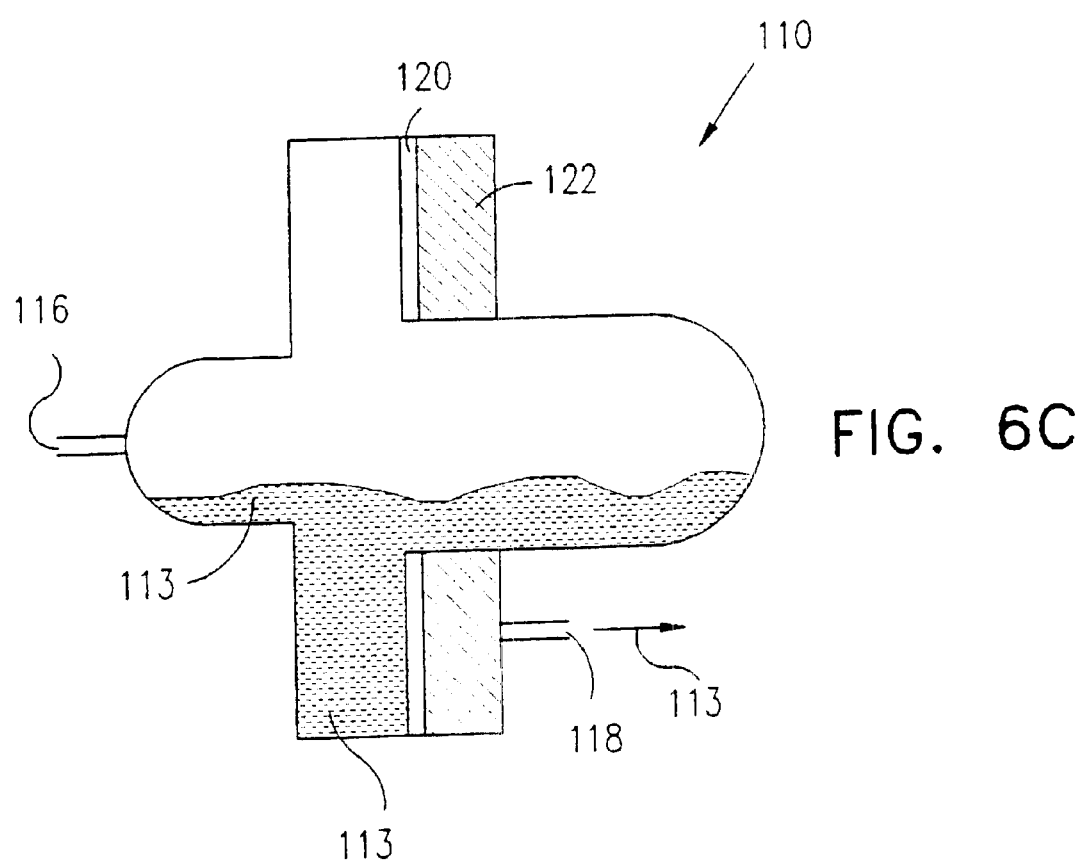

FIG. 6B illustrates the housing 110 in an upside-down orientation, and due to the contact of the liquid 113 with the membrane 120, liquid flow is maintained through the outlet 118. FIG. 6C further demonstrates that liquid flow is also maintained from the housing 110, with the housing 110 positioned in a generally horizontal orientation.

In accordance with another preferred embodiment of the present invention, the infusion liquid 113 is supplied to the narrow liquid inlet 116, providing small drops 132 in relatively quick succession (FIG. 5), thus enabling the observation of flow rates as low as 0.5 ml/hr. For example, an inlet tube of an inner diameter of 0.2 mm may be employed.

Figure 7:
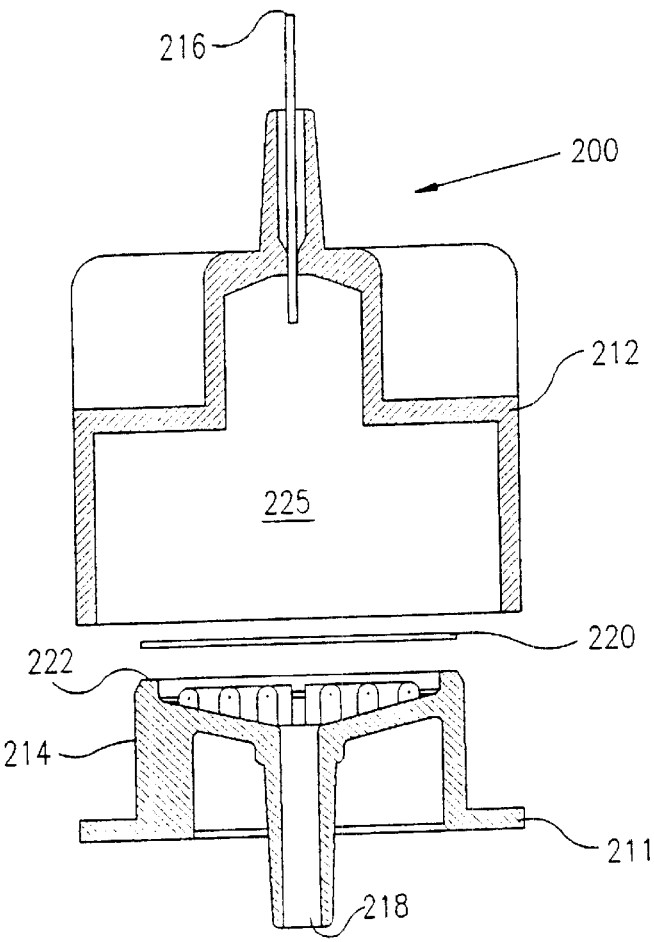
FIG. 7 is an exploded view pictorial illustration of an infusion flow indicator constructed and operative in accordance with yet another preferred embodiment of the present invention.
Figure 8:
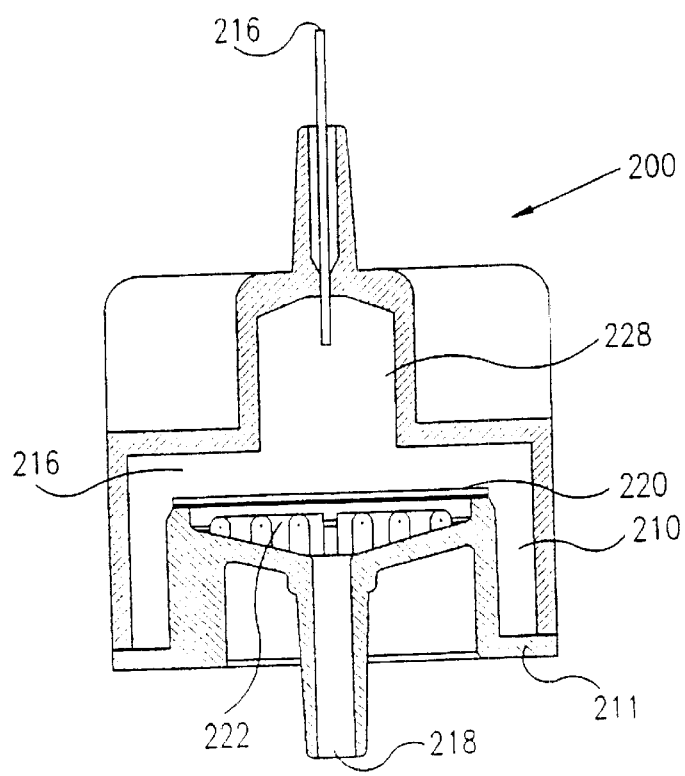
FIG. 8 is a sectional illustration of the assembled flow indicator of FIG. 7.

Reference is now made to FIG. 7, which is an exploded view of an infusion flow indicator constructed and operative in accordance with yet another preferred embodiment of the present invention and to FIG. 8, which is a sectional illustration of the flow indicator of FIG. 7.

The flow indicator of FIGS. 7 and 8 preferably comprises a housing indicated generally by reference numeral 200, and comprising first and second elements 212 and 214. In this third embodiment, the second element 214 includes a shoulder portion 211 and the diameter of element 212 is chosen so as to define a circumferential gap 210 when the first element 212 and the second element 214 are sealingly joined together, as illustrated in FIG. 8. The membrane 220 is sealingly joined to a membrane support 222.

Figure 9:
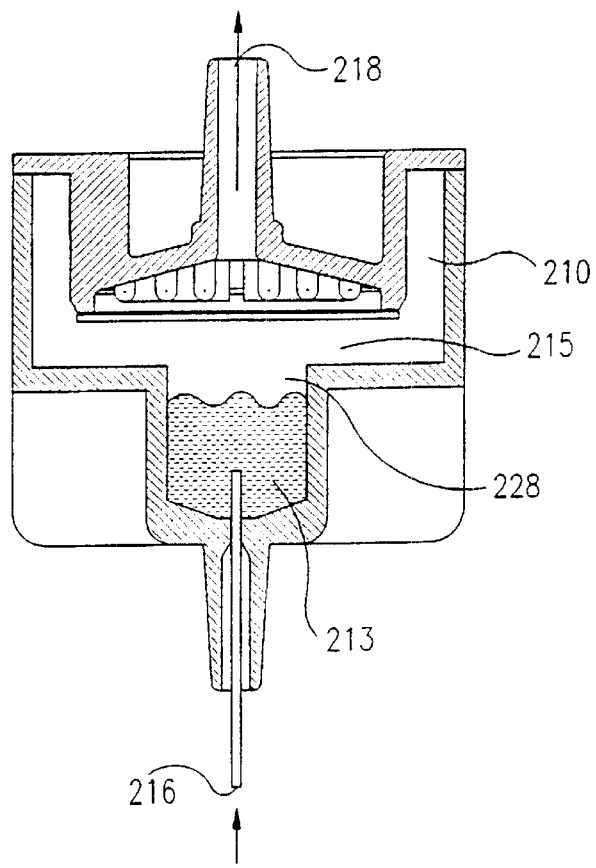
FIG. 9 is a sectional illustration of the flow indicator of FIGS. 7 and 8 during priming.
Figure 10:
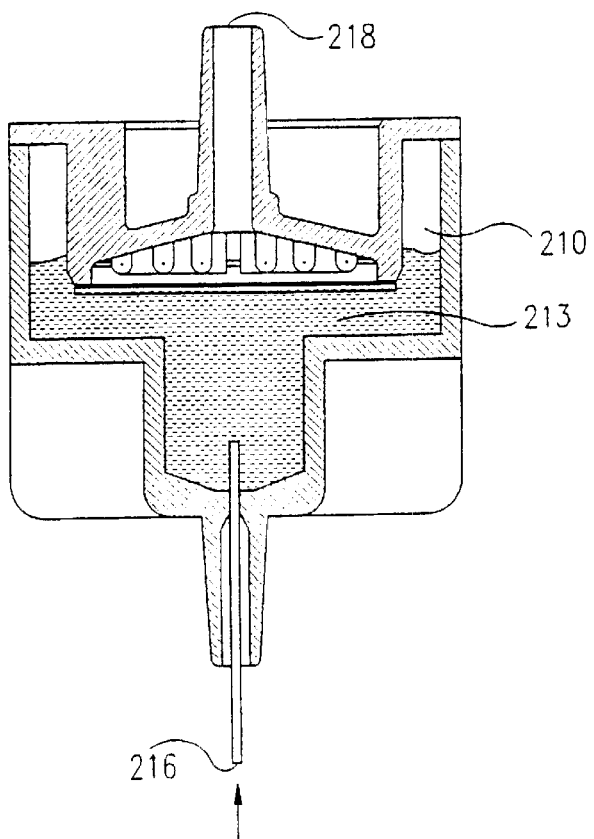
FIGS. 10 is an illustration of the flow indicator of FIGS. 7 and 8, fully primed.

Reference is now made to FIG. 9 which shows the priming operation of the present embodiment. The priming operation is carried out with the housing 200 of the flow indicator in an upside-down orientation. In the priming operation, the infusion liquid 213 enters the liquid inlet 216 and fills the volume 228. As the liquid level in the volume 228 rises, air escapes through the membrane 220 until the liquid 213 touches and fully wets the membrane 220. FIG. 10 illustrates the flow indicator in a fully primed condition, in which the residual air in circumferential gap 210 is compressed and the liquid 213 occupies about 40% of the volume 225.

Figure 11:
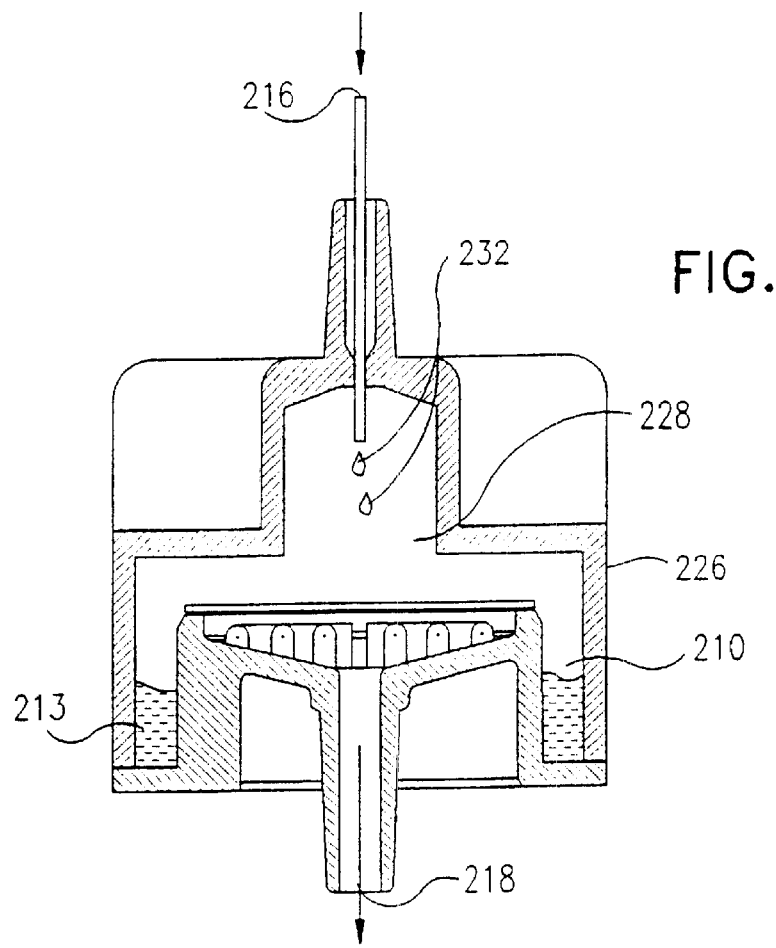
FIGS. 11 is an illustration of the flow indicator of FIGS. 7 and 8, in operation.

On turning the flow indicator to its upright operating position, FIG. 11, liquid drops 223 are visibly formed in volume 228. The infusion liquid flows through the membrane 220 and exits the flow indicator through outlet 218.

The infusion liquid 213 is supplied to the narrow liquid inlet 216, providing small drops 232 in relatively quick succession, thus enabling the observation of flow rates as low as 0.5 ml/hr. For example, an inlet tube of an inner diameter of 0.2 mm may be employed.

Figure 12:
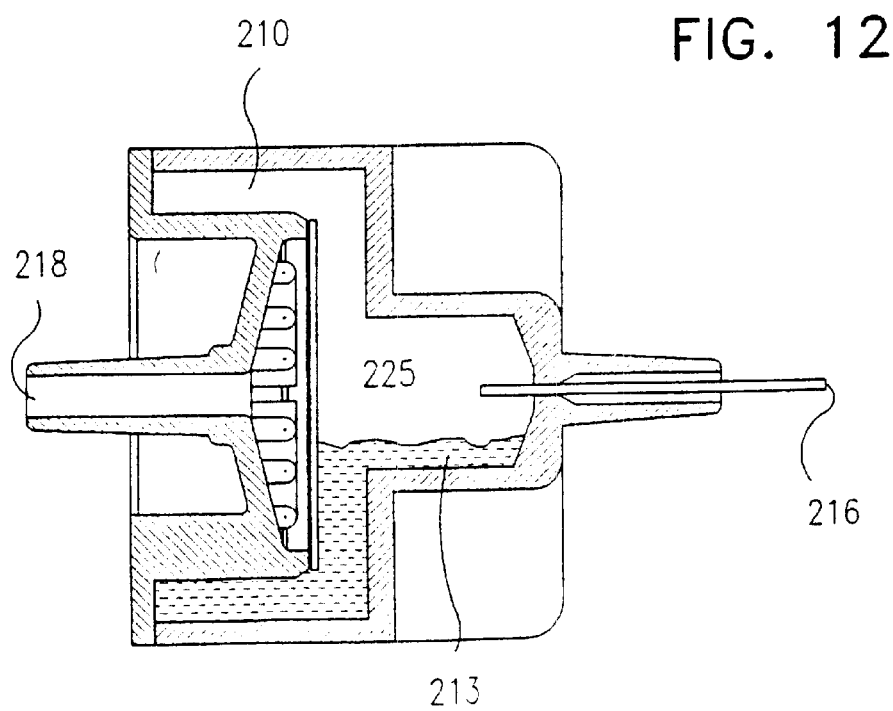
FIG. 12 is an illustration of the flow indicator of FIGS. 7 and 8, following priming, in a generally horizontal orientation.

Reference is now made to FIG. 12 which illustrates the flow indicator in a generally horizontal orientation with the infusion liquid 213 remaining in contact with the membrane 220.

It will be appreciated by persons skilled in the art that the present invention is not limited by what has been particularly shown and described hereinabove. Variations, combinations and subcombinations of features shown and described hereinabove are intended to fall within the scope of the present invention.

What is claimed is:

1. An intravenous infusion flow indicator comprising a housing defining an infusion liquid inlet and an infusion Liquid outlet, and a hydrophilic membrane disposed in the housing and being operative, when wetted, for permitting liquid flow and preventing air flow therethrough to the liquid outlet, wherein said housing comprises a droplet forming element and a droplet viewing volume, said droplet viewing volume being configured to remain at least partially filled with air, wherein when said housing is right side up said liquid flow may be observed as droplets in said droplet viewing volume, and wherein said membrane partitions said liquid inlet from said liquid outlet to constrain the liquid flow to follow a path from said liquid inlet through said membrane to said liquid outlet wherein the liquid flow cannot exit said housing by bypassing said membrane, and wherein said membrane is juxtaposed to said liquid inlet such that following priming, even when said housing is upside down, infusion liquid within the housing is always in touching relationship with the membrane, thereby permitting continued infusion liquid flow therethrough.

2. An intravenous infusion flow indicator according to claim 1 and wherein said membrane has a generally ring shape, the first volume and second volumes have generally semi-ellipsoidal configurations and the second volume is generally of larger size than the first volume.

3. An intravenous infusion flow indicator according to claim 2 and wherein said infusion liquid is supplied to the liquid inlet via narrow diameter tubing, providing small drops in relatively quick succession, thus enabling observation of flow rates as low as 0.5 ml/hr.

4. An intravenous infusion flow indicator according to claim 1 and wherein the housing defines first and second volumes communicating with each other, the first volume being greater than the second volume, the configuration and the sizes of the first and second volumes being selected such that when the housing is in an upright configuration, the second volume is generally filled with air such that drops falling therethrough can be readily viewed for monitoring.

5. An intravenous infusion flow indicator according to claim 1 and wherein said membrane has a generally disc shape, the first volume has a generally flat cylindrical configuration and the second volume has a generally cylindrical configuration which is narrower and taller than the first volume.

6. An intravenous infusion flow indicator according to claim 1 and wherein said membrane has a generally ring shape, the first volume has a generally top hat shape including a narrow high portion and a broad flat portion adjacent the membrane and the second volume has a generally cylindrical configuration similar to that of the narrow high portion.

7. An intravenous infusion flow indicator according to claim 1 and wherein said infusion liquid is supplied to the liquid inlet via narrow diameter tubing, providing small drops in relatively quick succession, thus enabling observation of flow rates as low as 0.5 ml/hr.

8. An intravenous infusion flow indicator according to claim 1 and wherein said membrane has a generally ring shape, the first volume has a generally semi-ellipsoidal shape and a broad flat portion adjacent the membrane and the second volume has a generally semi-ellipsoidal configuration.

9. An intravenous infusion flow indicating method comprising:

providing a housing defining an infusion liquid inlet and an infusion liquid outlet, and a hydrophilic membrane disposed in the housing and being operative, when wetted, for permitting liquid flow and preventing air flow therethrough to the liquid outlet, wherein said housing comprises a droplet forming element and a droplet viewing volume, said droplet viewing volume being configured to remain at least partially filled with air, wherein when said housing is right side up said liquid flow may be observed as droplets in said droplet viewing volume, and wherein said membrane partitions said liquid inlet from said liquid outlet to constrain the liquid flow to follow a path from said liquid inlet through said membrane to said liquid outlet wherein the liquid flow cannot exit said housing by bypassing said membrane, and wherein said membrane is juxtaposed to said liquid inlet such that following priming, even when said housing is upside down, infusion liquid within the housing is always in touching relationship with the membrane, thereby permitting continued infusion liquid flow therethrough;

priming said membrane with infusion liquid for full wetting thereof; and supplying infusion liquid under controlled pressure via said housing and said membrane to a patient.

10. An intravenous infusion flow indicating method according to claim 9 and wherein the housing defines first and second volumes communicating with each other, the first volume being greater than the second volume, the configuration and the sizes of the first and second volumes being selected such that when the housing is in an upright configuration, the second volume is generally filled with air such that drops falling therethrough can be readily viewed for monitoring.

11. An intravenous infusion flow indicating method according to claim 9 and wherein said membrane has generally disc shape, the first volume has a generally flat cylindrical configuration and the second volume has a generally cylindrical configuration which is narrower and taller than the first volume.

12. An intravenous infusion flow indicating method according to claim 9 and wherein said membrane has a generally ring shape, the first volume has a generally top hat shape including a narrow high portion and a broad flat portion adjacent the membrane and the second volume has a generally cylindrical configuration similar to that of the narrow high portion.

13. An intravenous infusion flow indicating method according to claim 9 and wherein said infusion liquid is supplied to the liquid inlet via narrow diameter tubing, providing small drops in relatively quick succession, thus enabling observation of flow rates as low as 0.5 ml/hr.

14. An intravenous infusion flow indicating method according to claim 9 and wherein said membrane has generally ring shape, the first volume has a generally semi-ellipsoidal configuration and the second volume has a generally semi-ellipsoidal configuration.

15. An intravenous infusion flow indicating method according to claim 9 and wherein said membrane has a generally ring shape, the first volume has a generally semi-ellipsoidal shape and a broad flat portion adjacent the membrane and the second volume has a generally semi-ellipsoidal configuration.

16. An intravenous infusion flow indicating method according to claim 9 and wherein said infusion liquid is supplied to the liquid inlet via narrow diameter tubing, providing small drops in relatively quick succession, thus enabling the observation of flow rates as low as 0.5 ml/hr.

* * * * *